United States Patent
Lane

(10) Patent No.: US 10,130,276 B2
(45) Date of Patent: Nov. 20, 2018

(54) MEDICAL APPARATUS

(71) Applicant: Chona Lane, Opelika, AL (US)

(72) Inventor: Chona Lane, Opelika, AL (US)

(73) Assignee: Emmanual, LLC, Opelika, AL (US)

( * ) Notice: Subject to any disclaimer, the term of this patent is extended or adjusted under 35 U.S.C. 154(b) by 17 days.

(21) Appl. No.: 14/453,411

(22) Filed: Aug. 6, 2014

(65) Prior Publication Data

US 2016/0038052 A1    Feb. 11, 2016

(51) Int. Cl.
*A61B 5/0428* (2006.01)
*A61B 5/0402* (2006.01)

(52) U.S. Cl.
CPC ........ *A61B 5/04286* (2013.01); *A61B 5/0402* (2013.01); *A61B 2560/0406* (2013.01); *A61B 2562/227* (2013.01)

(58) Field of Classification Search
CPC .................................................. A61B 5/0428
See application file for complete search history.

(56) References Cited

U.S. PATENT DOCUMENTS

| 3,821,496 | A | 6/1974 | Malone |
| 3,964,490 | A | 6/1976 | Nelms |
| 4,722,494 | A | 2/1988 | Fairchild |
| 5,033,474 | A | 7/1991 | Varelis et al. |
| 5,813,979 | A * | 9/1998 | Wolfer ............... A61B 5/04286 600/373 |
| 6,077,108 | A | 6/2000 | Lorscheider et al. |
| 6,205,355 | B1 | 3/2001 | Lomanto et al. |
| 6,327,507 | B1 | 12/2001 | Buchan |
| 7,039,460 | B2 | 5/2006 | Ryczek |
| 7,335,053 | B2 | 2/2008 | Avevor et al. |
| 8,571,627 | B2 | 10/2013 | Tremblay et al. |
| 2008/0265076 | A1 | 10/2008 | Petteys |
| 2010/0217113 | A1 * | 8/2010 | Jenkins ............... A61B 5/0002 600/411 |
| 2012/0022387 | A1 * | 1/2012 | Balda .................. A61B 5/0006 600/523 |

* cited by examiner

*Primary Examiner* — Carl H Layno
*Assistant Examiner* — Jennifer Ghand
(74) *Attorney, Agent, or Firm* — Thomas G. Peteerson; Maynard Cooper & Gale

(57) ABSTRACT

An apparatus comprising a plurality of electrically conductive elements for transmitting an electrical signal from a sensor to a medical device is described, wherein the electrically conductive elements are moveable between a first stored position and a second in use position. In this manner the apparatus provides an interface between the sensor and the medical device such that the length of each of the electrically conductive elements can be varied and adjusted such that the excess amount of the elements is minimized and the functionality of the sensors and/or medical device maximized.

17 Claims, 8 Drawing Sheets

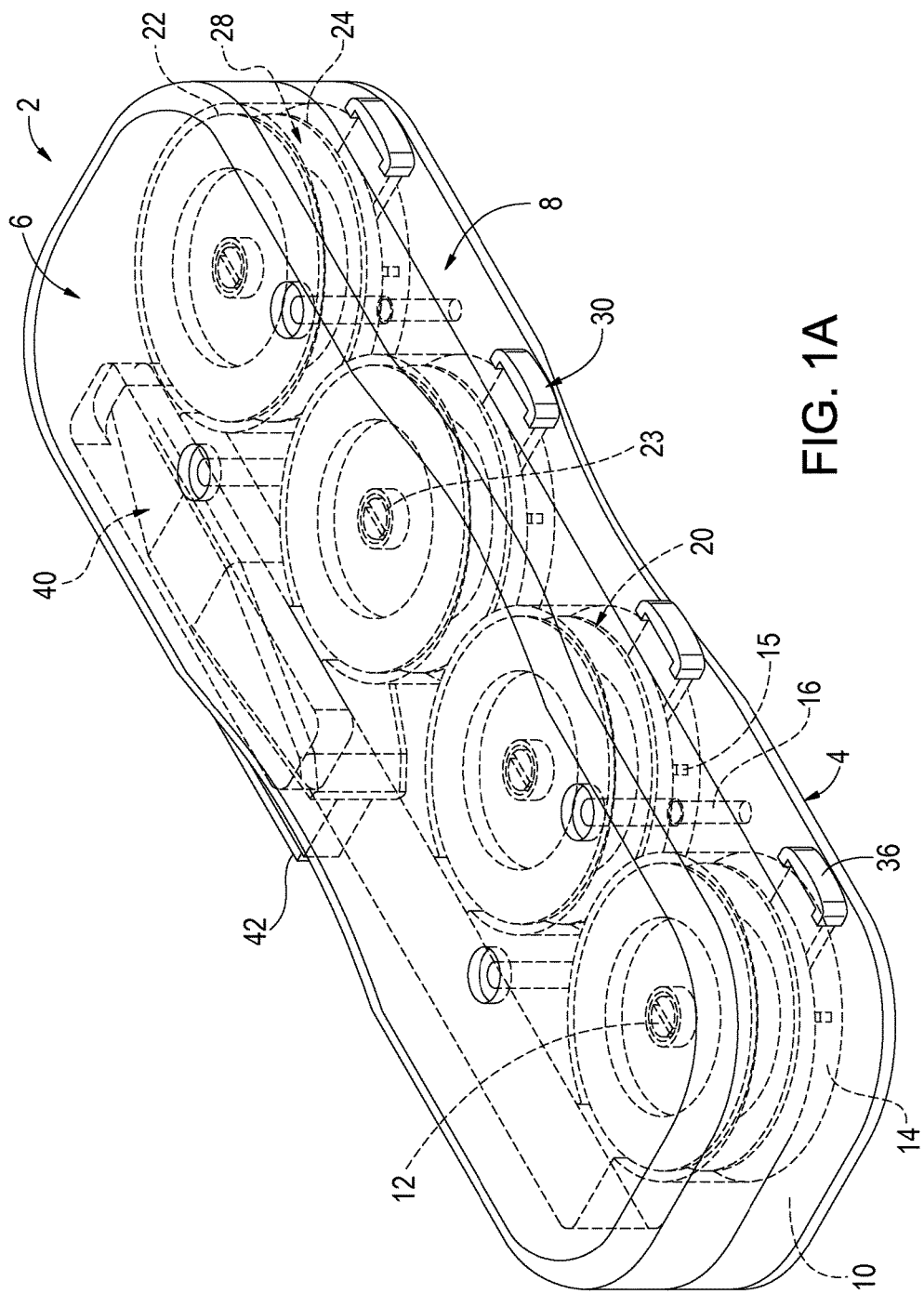

MEDICAL APPARATUS

BACKGROUND

The use of medical equipment and monitors to determine the condition of a subject or patient in the medical profession is increasing. Typically, such equipment includes one or more sensors to measure a characteristic of the patient and a medical device, such as a monitoring device. The sensors are placed in communications with the relevant piece of medical equipment to allow the signal detected by the sensor to be transmitted to the medical equipment. The signal detected is in many cases an electrical signal.

For example, electrocardiography (ECG or EKG) is the recording of the electrical activity of the heart. The output, which comprises a line timed graph tracing of the transmitted electrical activity of the heart, is referred to an electrocardiogram. In operation, several electrodes are placed on the body of the patient, typically on the skin of the chest, arms and legs. The electrodes are generally secured to the patient's skin with an adhesive pad. Each electrode is in electrical communication with the first end of a wire and the second end of the wire is in electrical communication with the electrocardiography equipment. As such, the electrical activity of the heart is detected by the electrodes and transformed by the electrocardiography equipment into a waveform graphed tracing for review by a medical professional. Typically, the electrocardiography equipment is placed next to the patient or is placed on the person of the patient (such as in a portable pouch). The optimal lengths of the wires that electrically connect the electrodes and the equipment vary depending on the particular application and the individual body size. However, in most cases, the equipment manufacturer provides cables or wires of a fixed length, typically 2-3 feet in length.

In many situations, the length of the wires is greater than required, resulting in excess length of the wires. This excess length can be detrimental. For example, due to the excess length of the wires, it is common for the wires to become tangled and unsteady. Furthermore, entanglement of the wires can cause the electrodes to become detached from the skin, requiring intervention from a medical professional to reattach the electrode. In such an instance, mistakes can be made reattaching the electrodes to the original configuration. These events consume time and cause delays in performing procedures, tests and monitoring the EKG.

The excess length can also cause the wires to move randomly when in use. When the wires are moving randomly, electrical interference and artifacts increase. Destabilization of the wires changes electrode adherence to the skin, which increases artifacts from muscles or limb movement and increases artifact from adipose tissue movement.

The excess length of the wire may lead to tangling as the patient moves causing the wire and the electrodes to become detached from the skin. This requires intervention from the central monitor to the alert caregiver of a possible emergency or intervention from a medical professional to reattach the electrode. The excess length and instability of wires also causes hindrance of movement to the patients.

Furthermore, the excess length of the wires may become entangled with the wires of lines of other pieces of medical equipment, exacerbating the effects discussed above. In addition, for the post-operative patient, increased pain occurs when the length and weight of wires move on the skin of the chest and abdominal incisions that may be tender after surgery.

The issues above cause a number of undesired results such as increased anxiety to the patient, interference with the transmitted electrical signals, artifacts on the EKG record, requirement for additional testing, incorrect diagnoses, increased billing or denial of insurance reimbursements and test performance delays. The foregoing contributes to difficulty reading to report the correct rhythm or analyze the rhythm changes. As a result, medical care may be impacted.

It would be beneficial to provide a device for controlling the length of the wires that connect the sensor to the medical equipment. Such a device would significantly reduce or eliminate the problems known with the prior art devices. The present disclosure provides a new apparatus for connecting the electrode and a piece of medical equipment that allows the weight and length of each individual wire to be independently controlled and thereby eliminates the problems previously mentioned.

BRIEF DESCRIPTION OF THE FIGURES

FIG. 1A shows a perspective view of one embodiment of the device.

SUMMARY OF THE INVENTION

Figure 1B:
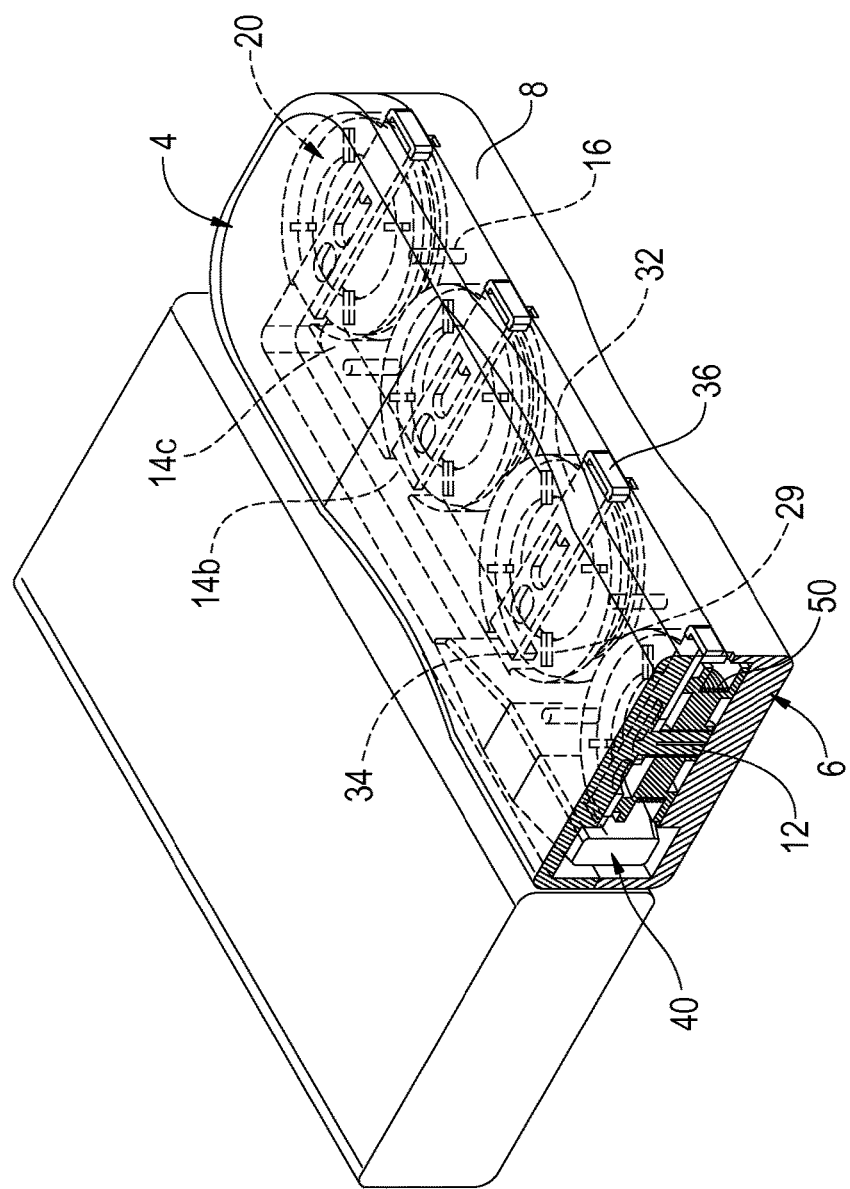
FIG. 1B shows a partial cutaway view of one embodiment of the device from the bottom perspective.

In a first aspect, the present disclosure provides an apparatus for conveying electrical signals, the apparatus comprising two or more electrically conductive elements for transmitting the electrical signal, wherein each electrically conductive element is independently moveable between a first stored position and a second in use position.

In a second aspect, the present disclosure provides an apparatus for conveying electrical signals, the apparatus comprising two or more electrically conductive elements for transmitting the electrical signal and a housing defining an interior space, wherein each electrically conductive element is stored, at least partially, within the housing and each electrically conductive element is independently moveable between a first stored position and a second in use position.

In a third aspect, the present disclosure provides an apparatus for conveying electrical signals, the apparatus comprising two or more electrically conductive elements for transmitting the electrical signal, a housing defining an interior space and a primary retraction element associated with each electrically conductive element for movably retaining each electrically conductive element, wherein each electrically conductive element is independently moveable between a first stored position and a second in use position.

In a fourth aspect, the present disclosure provides an apparatus for conveying electrical signals, the apparatus comprising two or more electrically conductive elements for transmitting the electrical signal, a housing defining an interior space and a primary retraction element associated with each electrically conductive element for movably retaining each electrically conductive element, wherein the primary retraction element is located within the interior space and each electrically conductive element is independently moveable between a first stored position and a second in use position.

In a fifth aspect, the present disclosure provides an apparatus for conveying electrical signals, the apparatus comprising two or more electrically conductive elements for transmitting the electrical signal, a housing defining an interior space, the housing having at least a first and second opposed faces and at least one opening for the electrically conductive elements, and a primary retraction element associated with each electrically conductive element for movably retaining each electrically conductive element, wherein the primary retraction element is located within the interior space and each electrically conductive element is independently moveable between a first stored position and a second in use position.

In a sixth aspect, in any of the device of the first through fifth aspects, at least one of the electrically conductive elements is a primary group, the primary group comprising a plurality of primary electrically conductive elements, wherein the primary electrically conductive elements of the primary group are movable between the first stored position and the second in use position as a group so that a user is only required to position the primary group to position the plurality of primary electrically conductive elements to reach the in use position.

In a seventh embodiment, in a device of the sixth aspect, the primary group further comprises an intermediate retraction element, wherein the primary electrically conductive elements of the primary group are movable between the first stored position and an intermediate position as a group and between the intermediate position and the second in use position individually so that a user is only required to position the single primary group to the intermediate position and the individual primary electrically conductive elements to reach the in use position.

In any of the foregoing aspects, the electrically conductive elements are movable between a first stored position and a second in use position. In the stored position, the electrically conductive elements are stored by the primary retraction element. The electrically conductive element may be stored completely within the housing or a portion may extend outside the housing. In the in-use position, the electrically conductive elements are removed from the housing by the action of a user to a desired position and length for use on a subject. The action of a user, in one embodiment, is the pulling of the electrically conductive elements from the housing. The action of the user may further comprise positioning the electrically conductive element for use and/or the attachment to an electrode.

In any of the foregoing aspects comprising a primary group, the primary group comprises 2 primary electrically conductive elements, 3 primary electrically conductive elements, 4, primary electrically conductive elements or 5 or more primary electrically conductive elements. In another embodiment, the primary electrically conductive elements are adapted to be positioned on a subject in an area group, such as, but not limited to, the torso of the subject. The device may have 1 primary group, 2 primary groups or 3 or more primary groups.

In any of the foregoing aspects comprising a primary group, the primary group may further comprise an intermediate retraction element. In one embodiment of this aspect, the primary electrically conductive elements of the primary group are movable between the first stored position and an intermediate position as a group and between the intermediate position and the second in use position individually so that a user is only required to position the single primary group to the intermediate position and the individual primary electrically conductive elements to reach the in use position. In one embodiment, the primary group comprises 2 primary electrically conductive elements, 3 primary electrically conductive elements, 4, primary electrically conductive elements or 5 or more primary electrically conductive elements. In another embodiment, the primary electrically conductive elements are adapted to be positioned on a subject in an area group, such as, but not limited to, the torso of the subject. The device may have 1 primary group, 2 primary groups or 3 or more primary groups.

In any of the foregoing aspects, the primary retraction element may comprise a base, the base having an interior channel bounded, at least partially, by two opposing guide flanges. The electrically conductive elements are retained by the base and a portion of the electrically conductive elements wrap around the base and are contained by the interior channel and guide flanges. A portion of the electrically conductive elements extend beyond the primary retraction element at both the first and second ends, with the first and second ends adapted to be in electrical communication with a sensor and an output, respectively. Furthermore, in one embodiment, the primary retraction element is adapted for rotational movement about a central member within the interior and is in communication with a biasing element which biases the primary retraction element and the associated electrically conductive element towards the first stored position.

In any of the foregoing aspects, the apparatus or device may further comprise a stop element. In one embodiment, the stop element is a ratchet stop that allows the primary retraction element to rotate in a single direction and prevents counter-rotation of the primary retraction element. However, any mechanism that prevents such counter-rotation may be used. Furthermore, the primary retraction element may comprise a release mechanism to disengage the stop element and allow the primary retraction element to counter-rotate.

In any of the foregoing aspects, the sensor may be any sensor known in the art. In a particular embodiment, the sensor is an electrode.

In any of the foregoing aspects, the output transmits the electrical signal to a monitoring device. The output may transmit the signal to the monitoring device by any means known in the art. In one embodiment, the output transmits the electrical signal via wireless communication. In another embodiment, the output transmits the electrical signal via a transfer cable. The monitoring device may be any monitoring device known in the art. In one embodiment the monitoring device is an electrocardiograph.

In any of the foregoing aspects, the apparatus or device may comprise two electrically conductive elements, three electrically conductive elements, four electrically conductive elements, five electrically conductive elements, six electrically conductive elements, seven electrically conductive elements, eight electrically conductive elements, nine electrically conductive elements or ten or more electrically conductive elements. In one particular embodiment of the foregoing aspects, the apparatus or device comprises between 3 and 10 electrically conductive elements, between 5 and 10 electrically conductive elements or between 3 and 7 electrically conductive elements. Any of the electrically conductive elements may be part of a primary group as described herein.

In any of the foregoing aspects, the electrically conductive elements may be coded for ease of use by a user of the apparatus or device. Any system of coding may be used. In one embodiment, the coding system is color coding. In this embodiment, each electrically conductive element may display a particular color along at least a portion of its length to specify the correct anatomical placement on a subject based on standard EKG operating procedures. In another embodiment, the coding system is tactile based. In this embodiment, each electrically conductive element may have a particular shape or texture along at least a portion of its length to specify the correct placement on a subject.

In any of the foregoing aspects, the apparatus may be a part of a medical device, such as a monitoring device. In such an embodiment, the housing of the apparatus may form a portion of the housing of the medical device or the housing may be eliminated and the components described above may be positioned in the interior of the medical device. In such an embodiment, the medical device incorporates the features of the apparatus described above.

DETAILED DESCRIPTION

In the most general sense, the present disclosure provides an apparatus comprising a plurality of electrically conductive elements for transmitting an electrical signal from a sensor to a medical device, wherein the electrically conductive elements are moveable between a first stored position and a second in use position. In this manner the apparatus provides an interface between the sensor and the medical device such that the length of the electrically conductive elements can be varied and adjusted such that the excess amount of the elements is minimized and the functionality of the sensors and/or medical device maximized.

The apparatus of the present disclosure may have a number of different configurations. In one embodiment, the present disclosure provides an apparatus for conveying electrical signals, the apparatus comprising two or more electrically conductive elements for transmitting the electrical signal, wherein each electrically conductive element is independently moveable between a first stored position and a second in use position.

In another embodiment, the present disclosure provides an apparatus for conveying electrical signals, the apparatus comprising two or more electrically conductive elements for transmitting the electrical signal and a housing defining an interior space, wherein each electrically conductive element is stored, at least partially, within the housing and each electrically conductive element is independently moveable between a first stored position and a second in use position.

In still another embodiment, the present disclosure provides an apparatus for conveying electrical signals, the apparatus comprising two or more electrically conductive elements for transmitting the electrical signal, a housing defining an interior space and a primary retraction element associated with each electrically conductive element for movably retaining each electrically conductive element, wherein each electrically conductive element is independently moveable between a first stored position and a second in use position.

In a further embodiment, the present disclosure provides an apparatus for conveying electrical signals, the apparatus comprising two or more electrically conductive elements for transmitting the electrical signal, a housing defining an interior space and a primary retraction element associated with each electrically conductive element for movably retaining each electrically conductive element, wherein the primary retraction element is located within the interior space and each electrically conductive element is independently moveable between a first stored position and a second in use position.

In yet a further embodiment, the present disclosure provides an apparatus for conveying electrical signals, the apparatus comprising two or more electrically conductive elements for transmitting the electrical signal, a housing defining an interior space, the housing having at least a first and second opposed faces and at least one opening for the electrically conductive elements, and a primary retraction element associated with each electrically conductive element for movably retaining each electrically conductive element, wherein the primary retraction element is located within the interior space and each electrically conductive element is independently moveable between a first stored position and a second in use position.

In still a further embodiment, the present disclosure provides an apparatus for conveying electrical signals, wherein at least one of the electrically conductive elements is a primary group, the primary group comprising a plurality of primary electrically conductive elements, wherein the primary electrically conductive elements of the primary group are movable between the first stored position and the second in use position as a group so that a user is only required to position the primary group to position the plurality of primary electrically conductive elements to reach the in use position.

In still a further embodiment, the present disclosure provides an apparatus for conveying electrical signals, wherein at least one of the electrically conductive elements is a primary group, wherein the primary group further comprises an intermediate retraction element, wherein the primary electrically conductive elements of the primary group are movable between the first stored position and an intermediate position as a group and between the intermediate position and the second in use position individually so that a user is only required to position the single primary group to the intermediate position and the individual primary electrically conductive elements to reach the in use position.

Electrically Conductive Elements

The present disclosure provides a device wherein the electrically conductive elements are movable between a first stored position and a second in use position as well as a device wherein the electrically conductive elements are movable between a first stored position, an intermediate position and a second in use position. In this manner, the length of the electrically conductive elements may be adjusted as required by a particular application in order to minimize excess length and the problems that are inherent therein. In the stored position, the electrically conductive elements are stored, at least partially, within a housing. In certain embodiments, a portion of at least one of the electrically conductive elements extends outside the housing so as to be accessible to a user of the device. To place the electrically conductive elements in the in-use position, the electrically conductive elements are removed from the housing by the action of a user to a desired position and length for use on a subject. The action of a user, in one embodiment, is the pulling of the electrically conductive elements from the housing. The action of the user may further comprise positioning the electrically conductive element for use and/or the attachment to a sensor.

The electrically conductive elements may be any wires or lead wires that are known in the art. The only requirement for the electrically conductive elements is that they transmit the electrical signal received by the sensor to the medical device. Such electrical conductive elements, often called "lead wires" when used in conjunction with ECG procedures, are available from a number of suppliers. Electrically conductive elements with smaller diameters offer the advantage or more efficient packing and storage within the device, allowing the size of the device to be decreased. In one embodiment, the electrical conductive elements are manufactured in compliance with ANSI/AAMI EC53 requirements.

Each electrically conductive element has a first end and a second end. One of the first or second ends is in communication with a sensor as discussed herein. The other of the first or second ends is in communication with an output for carrying or transmitting the electrical signal to the medical device. In one embodiment, the portion of the electrically conductive element opposite the sensor extends to a connection point and is in communication with a conductive element to convey the electrical signal to the output. The conductive element of the connection point may be in further communication with an output wire to convey the electrical signal to the output or the conductive element of the connection point may be in direct electrical communication with the output. Such methods of connection are well known in the art.

The output may be separate electrically conductive element that is in electrical communication with the medical device. Further, the output may be a wireless transmitter that is in wireless communication with the medical device. Any form of output as is known in the art may be used with the device of the present disclosure.

The electrically conductive elements may further comprise a sensor for use with a subject. Furthermore, the electrically conductive elements may be supplied without an attached sensor, with one end of the electrically conductive element modified to allow a reversible attachment to a sensor. Such reversible attachment mechanisms include a snap-fit, button snaps, pinch clips, spring-loaded and the like. Any mechanisms for reversibly securing the electrically conductive element may be used. The type of sensor used will depend, at least in part, on the procedure being performed and/or on the medical device. Any sensor known in the art may be used. In one embodiment, the sensor is an ECG electrode.

The device of the present disclosure may comprise two electrically conductive elements, three electrically conductive elements, four electrically conductive elements, five electrically conductive elements, six electrically conductive elements, seven electrically conductive elements, eight electrically conductive elements, nine electrically conductive elements or ten electrically conductive elements, eleven electrically conductive element, twelve electrically conductive elements or more than twelve electrically conductive elements. In one particular embodiment of the foregoing aspects, the apparatus or device comprises between 3 and 12 electrically conductive elements, between 5 and 10 electrically conductive elements or between 3 and 7 electrically conductive elements. Any of the electrically conductive elements may be part of a primary group as described herein.

In one embodiment, at least one of the electrically conductive elements is a primary group. The primary group is a plurality of individual electrically conductive elements, referred to as primary electrically conductive elements, which are grouped together. Each primary electrically conductive element may be separate or may be grouped together. Regardless, each of the primary electrically conductive elements of the primary group carries its own electrical signal. In these embodiments, the primary electrically conductive elements of the primary group are movable between the first stored position and the in use position as a group so that a user is only required to position the single primary group reach the in use position. In one embodiment, the primary group comprises 2 primary electrically conductive elements, 3 primary electrically conductive elements, 4, primary electrically conductive elements or 5 or more primary electrically conductive elements. The device may have 1 primary group, 2 primary groups or 3 or more primary groups.

When one of the electrically conductive elements is a primary group, the primary group may further comprise an intermediate retraction element. The intermediate retraction element allows for further manipulation of the lengths of the primary electrically conductive elements that are a part of the primary group. In these embodiments, the primary electrically conductive elements of the primary group are movable between the first stored position and an intermediate position as a group and between the intermediate position and the second in use position individually so that a user is only required to position the single primary group to the intermediate position and the individual primary electrically conductive elements to reach the in use position. In one embodiment, the primary group comprises 2 primary electrically conductive elements, 3 primary electrically conductive elements, 4, primary electrically conductive elements or 5 or more primary electrically conductive elements. In another embodiment, the primary electrically conductive elements are adapted to be positioned on a subject in an area group, such as, but not limited to, the torso of the subject. The device may have 1 primary group, 2 primary groups or 3 or more primary groups.

In one embodiment, the primary electrically conductive elements, both with and without an intermediate retraction device, are adapted to be positioned on a subject in an area group, such as, but not limited to, the torso of the subject, the aims of a subject and the legs of a subject. When an intermediate retraction device is not present, the lengths of the primary electrically conductive elements may be the same or may be different. In the latter case, the lengths of the primary electrically conductive elements may be set to specific lengths based on the placement of the individual electrically conductive elements on the subject.

Furthermore, the electrically conductive elements, including those elements that may be part of a primary electrically conductive element, may be coded for ease of use by a user of the device. Any system of coding may be used. In one embodiment, the coding system is color coding, such as used by the American Heart Association or the International Electrotechnical commission. In this embodiment, each electrically conductive element may display a particular color along at least a portion of its length to specify the correct anatomical placement on a subject based on standard EKG operating procedures. Representative color coding systems are shown below.

| | AHA (American Heart Association) | | IEC (International Electrotechnical Commission) | |
|---|---|---|---|---|
| Location | Inscription | Colour | Inscription | Colour |
| Right Arm | RA | White | R | Red |
| Left Arm | LA | Black | L | Yellow |

-continued

| Location | AHA (American Heart Association) | | IEC (International Electrotechnical Commission) | |
|---|---|---|---|---|
| | Inscription | Colour | Inscription | Colour |
| Right Leg | RL | Green | N | Black |
| Left Leg | LL | Red | F | Green |
| Chest | V1 | Brown/Red | C1 | White/Red |
| Chest | V2 | Brown/Yellow | C2 | White/Yellow |
| Chest | V3 | Brown/Green | C3 | White/Green |
| Chest | V4 | Brown/Blue | C4 | White/Brown |
| Chest | V5 | Brown/Orange | C5 | White/Black |
| Chest | V6 | Brown/Purple | C6 | White/Violet |

In another embodiment, the coding system is tactile based. In this embodiment, each electrically conductive element may have a particular shape or texture along at least a portion of its length to specify the correct placement on a subject. Other forms of coding may also be used.

Housing

The apparatus described above may further comprise a housing to contain the electrically conductive elements and other elements of the apparatus. The housing may be of any shape desired. In one embodiment, the housing is an oval, a rectangle or a square. Whatever the overall shape of the housing, the housing is constructed to provide storage of the electrically conductive elements and other components of the apparatus. The housing may completely or partially enclose the electrically conductive elements. The housing further comprises an opening for the electrically conductive elements. The housing may comprise a single opening for the electrically conductive elements. Alternatively, the housing may comprise an opening for each electrically conductive element. It is understood that when an electrically conductive element is a primary electrical conductive element, a single opening may be present for the primary electrically conductive element.

In one embodiment, the housing is provided with contoured or rounded edges for comfort of the subject. In such an embodiment, the presence of angular edges is avoided, eliminating the possibility of the edges providing discomfort to the patient.

The housing may be constructed of any material known in the art. However, it is desirable to provide a housing that is constructed out of a lightweight material that is resistant to heat, chemical treatment (such as sterilizing agents and disinfectants), impact and wear. In additional, the material should by hypoallergenic. Exemplary materials include, but are not limited to, plastics and polymers. Exemplary materials include, but are not limited to, acetals, polyvinyl chlorides, ethylene-chlorotrifluoroethylene, urethane, polyvinylidene fluoride, polycarbonate, polyphenylene ether, nylon, polychlorotrifluoroethylene, polyetheretherketone, polyethersulfone, perfluoroalkoxy resins, polyethylene, polypropylene, polystyrene, polysulfone and polyethersulfone.

The housing defines an interior space in which the electrically conductive elements are stored, as well as other components of the device (for example, the retraction elements discussed herein). The interior space may completely or partially enclose the electrically conductive elements and other components. Furthermore, the housing may be specifically adapted to receive components of the device, such as the retraction elements.

In one embodiment, the housing comprises a base portion, a top portion and sidewalls that join, at least partially, the base portion and top portion. As discussed above, the sidewalls may further comprise one or more openings for the electrically conductive elements as well as openings for the stop elements (discussed below) and the output. In one embodiment, the housing comprises a receiving point for the retraction element. In a specific embodiment, the receiving point comprises a support member, such as a post, and may optionally comprise a recess matching the configuration of the retraction element; the recess may also contain the stop element for controlling rotation of the retraction element. In one embodiment, the retraction element is rotatable received by the support member. The housing may further comprise a channel or passageway for an output wire. As discussed herein, the output wire further carries the electrical signals to the output for transmission to the medical device. The output wire may be an extension of each electrically conductive element or may be a separate element.

Retraction Elements

The retraction elements allow for the electrically conductive elements to be adjusted to the minimum length required for use in a specific procedure. The retraction element may be any retraction element allowing for the controlled spooling and un-spooling of the electrically conductive elements. As discussed herein, the retraction element is received by and contained, at least partially, by the housing and stores, at least partially, the electrically conductive elements.

In one embodiment, the retraction element is a spring-biased retraction element. In a further embodiment, the retraction element is a circular spring-biased retraction element. In a particular embodiment, the retraction element contains an upper and lower base extending circumferentially about a central bore, the upper and lower based being connected by a central member that defines the diameter of the central bore, wherein the upper and lower bases and the central member define a channel for receiving the electrically conductive element. The central bore is adapted to rotatably interact with a support member or similar structure in the housing. A spring is connected to the retraction element, such as at the lower base or the central member at one end and attached to the housing at the other. In the storage position, the spring is biased to provide no rotation to the retraction device. When a user extends the electrically conductive elements, the retraction device rotates about the support member allowing the electrically conductive elements to be extended to the in-use position, introducing a bias into the spring that urges the retraction device to rotate in the opposite direction and return to the electrically conductive elements to the storage position.

When the electrically conductive elements are extended to the in-use position, the spring is tensioned urging the retraction of the electrically conductive elements. A stop element interacts with the retraction device to prevent the retraction of the electrically conductive elements until desired by the user. A variety of such stop elements are known in the art and any may be used. In one embodiment, the stop element is a ratchet type device comprising a base plate, the base plate having a release tab on one end a ratchet projection on the opposite end to reversibly interact with receiving structures position at defined intervals on the retraction element. As the retraction element is rotated by the extension of the electrically conductive elements (and tension is introduced into the spring), the ratchet projection serially engages the receiving structures and thereby prevents the opposite rotation of the retraction device allowing the electrically conductive element associated with the retraction device to remain extended and in the in use position. When it is desired to retract the electrically conductive, element to return it to the storage position, the release tab is activated, such as pressing in or down on the release tab, which prevents the ratchet projection from interacting with the receiving elements allowing the biased spring to rotate the retraction element in the opposite direction of the original rotation.

Description of Embodiment

While not meaning to limit the scope of the present disclosure to any particular embodiment, one embodiment of the device of the present disclosure is described herein to illustrate the principles of operation of the device. FIGS. 1-4 are referenced in this description.

FIG. 1A shows housing 2 comprising a base portion 4, a top portion 6 and sidewalls 8 defining an interior space 10. Base portion 4 further comprises a support member 12 and recess 14 for receiving the retraction element 20 (best shown in FIG. 2). The recess is at least partially defined by walls 14a; an opening, designated 14b may be present to allow the electrically conductive elements 50 to exit the recess 14 for interaction with the connection point and/or output. The recess 14 further comprises structures 15 for supporting the retraction element 20 and providing space for the stop element 30. Base portion 4 is shown comprising posts 16 at various locations to provide support for the housing. Posts 16 may be located at any desired position. The side walls 8 also comprise various openings 8A for the electrically conductive elements 50, the stop element 30 and the output 40. While FIG. 1 shows the retraction elements 20 in a side-by-side configuration, they may be present in any desired configuration, such s a vertical stack, without changing the principles of operation.

Figure 3A:
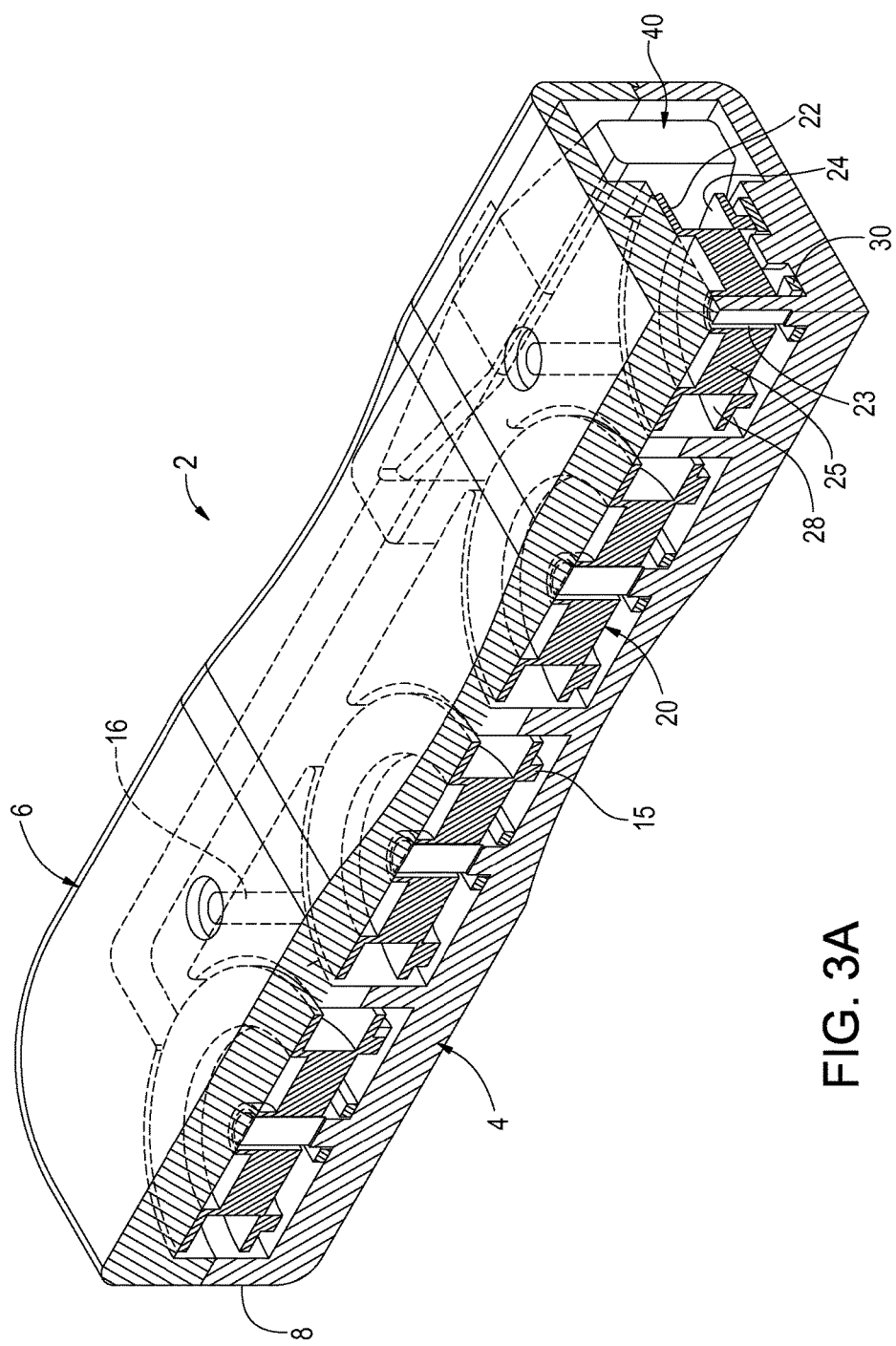
FIG. 3A shows a cutaway view of one embodiment of the device.
Figure 3B:
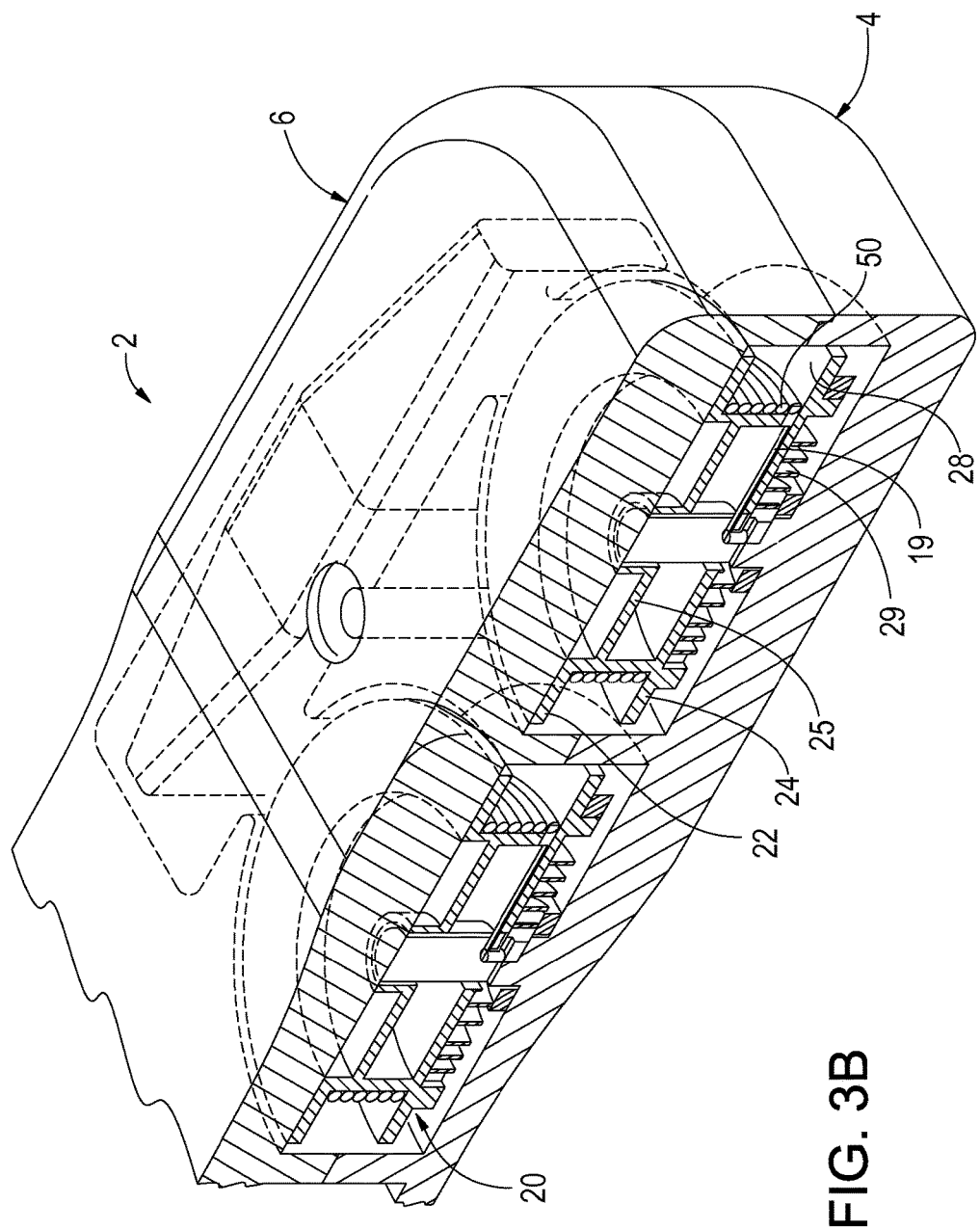
FIG. 3B shows a perspective view of one embodiment of the retraction element.

The retraction elements comprise an upper 22 and lower 24 base defining a channel 28 for receiving the electrically conductive element 50 and a central bore 23 defined by a central member 25 (best shown in FIGS. 1B and 3A). Spring 19 (best shown in FIG. 3B) is attached to the support member 12 on one end and the retraction element 20 on the opposite end. The stop element 30 is placed below the lower base 24 of the retraction element 20.

Figure 2A:
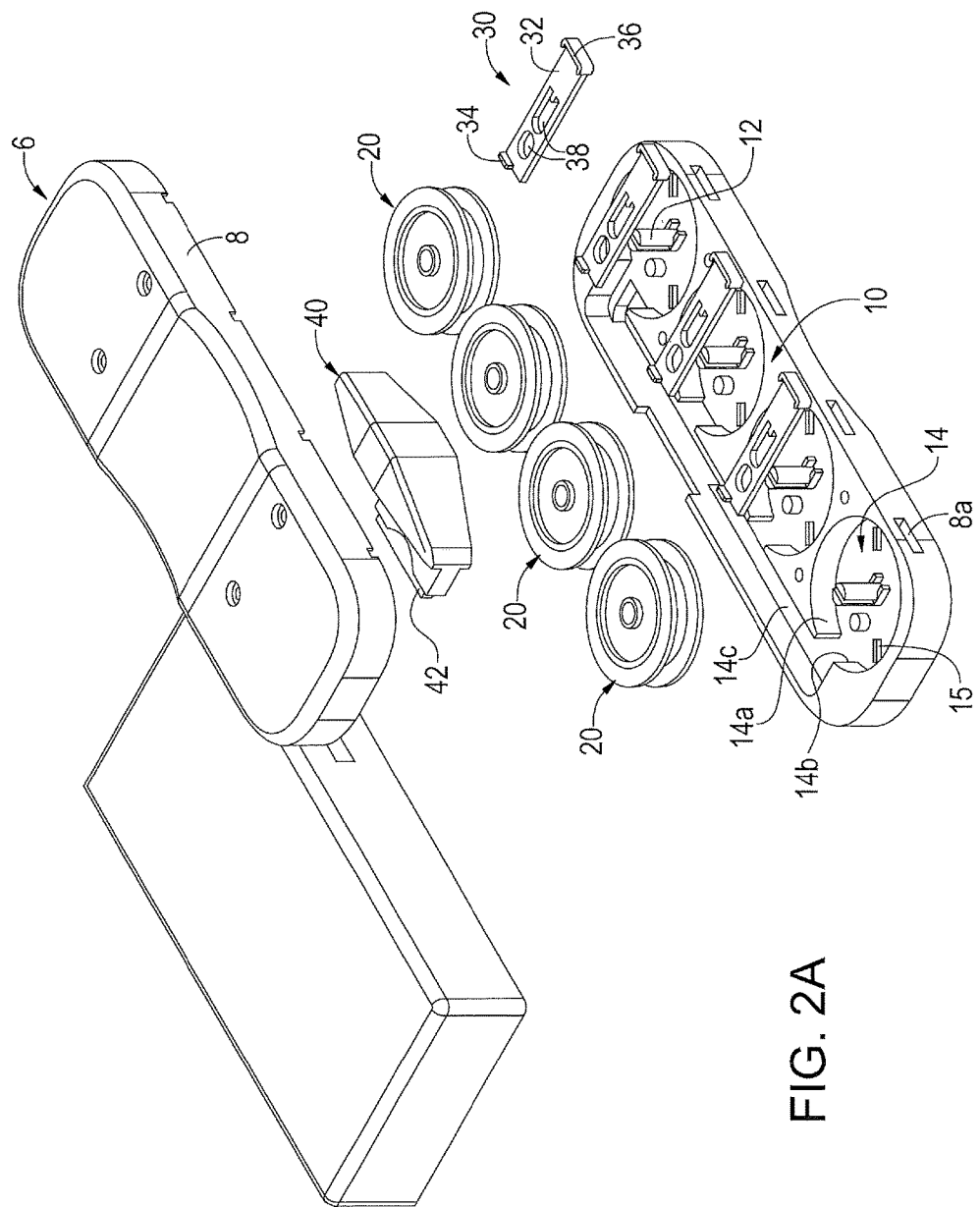
FIG. 2A shows an exploded view of one embodiment of the device.
Figure 2B:
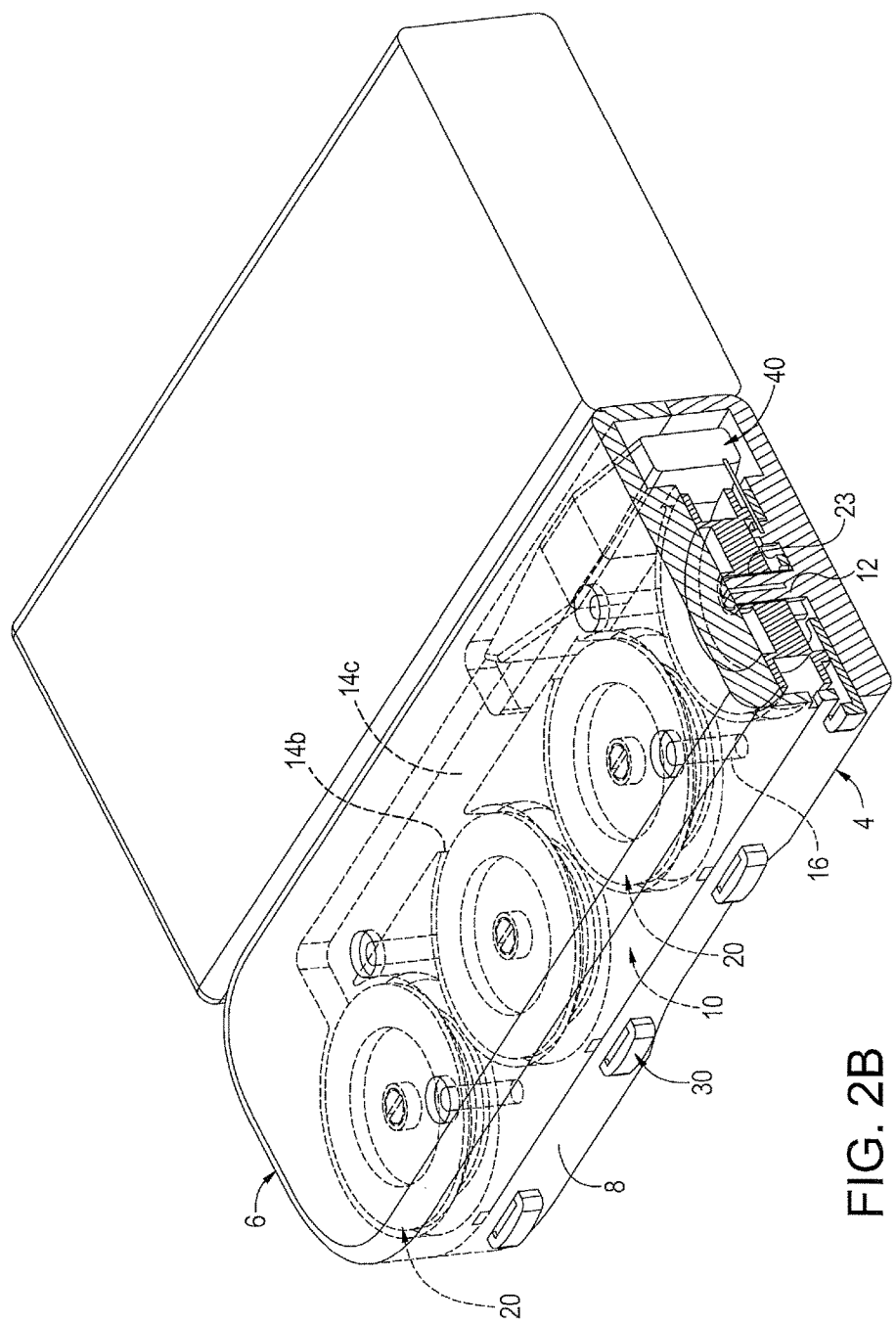
FIG. 2B shows a partial cutaway view of one embodiment of the device from the top perspective.

The stop element, best shown in FIGS. 1B and 2A, comprises a base plate 32, a ratchet projection 34 and a release tab 36. Stop element 30 may further comprise openings 38 to interact with structures on the base plate 4, such as the support member 12. The stop element 30 interacts with receiving elements 29 (best shown in FIGS. 1B and 3B) on the retraction element 20 when in the first position. As the retraction element rotates when the electrically conductive element is pulled from the housing 2, the action tensions spring 19. The interaction of the ratchet projection 34 with the receiving elements 29 prevents the spring from urging the retraction element to retract the electrically conductive element to its original position, allowing the electrically conductive element to be placed in the in use position. When the stop element 30 is urged into the second position by the action of a user the ratchet projection 34 is no longer in contact with the receiving elements 29, allowing the rotation of the retraction member to its original position The electrically conductive element comprises a first end that is adapted to reversible engage a sensor and a second end that is in communication with output 40, either directly or indirectly. The electrically conductive element 50 extend from the retraction element near the second end, exits the recess 14 through opening 14B and travels along passageway 14C. The electrically conductive elements 50 are in electrical communication with a connection point, designated 42, on the output 40. The output 40 conveys the electrical signals to the medical device as is known in the art.

Figure 4A:
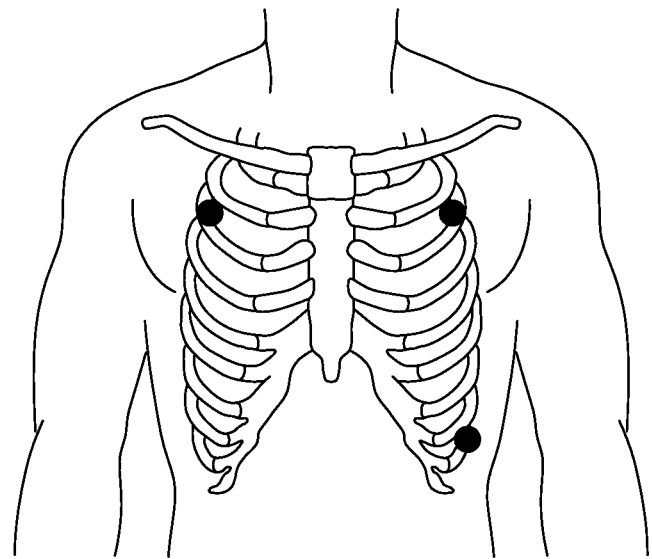
FIG. 4A shows illustrative placement of ECG electrodes for a 3 electrode system.
Figure 4B:
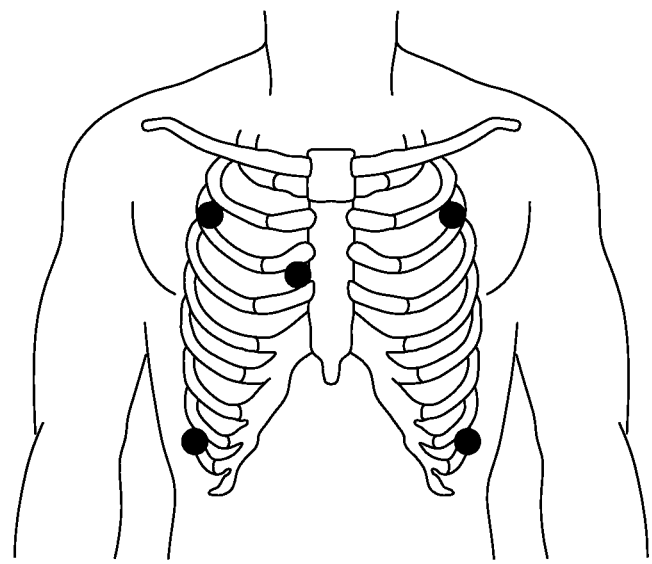
FIG. 4B shows illustrative placement of ECG electrodes for a 5 electrode system.

The first end of the retraction elements are placed at the in use position by the action of a user. The in use position may vary depending on the procedure being performed. Exemplary in use positions for a 3 and 5 lead ECG system are shown in FIGS. 4A and B, respectively.

Figure 5:
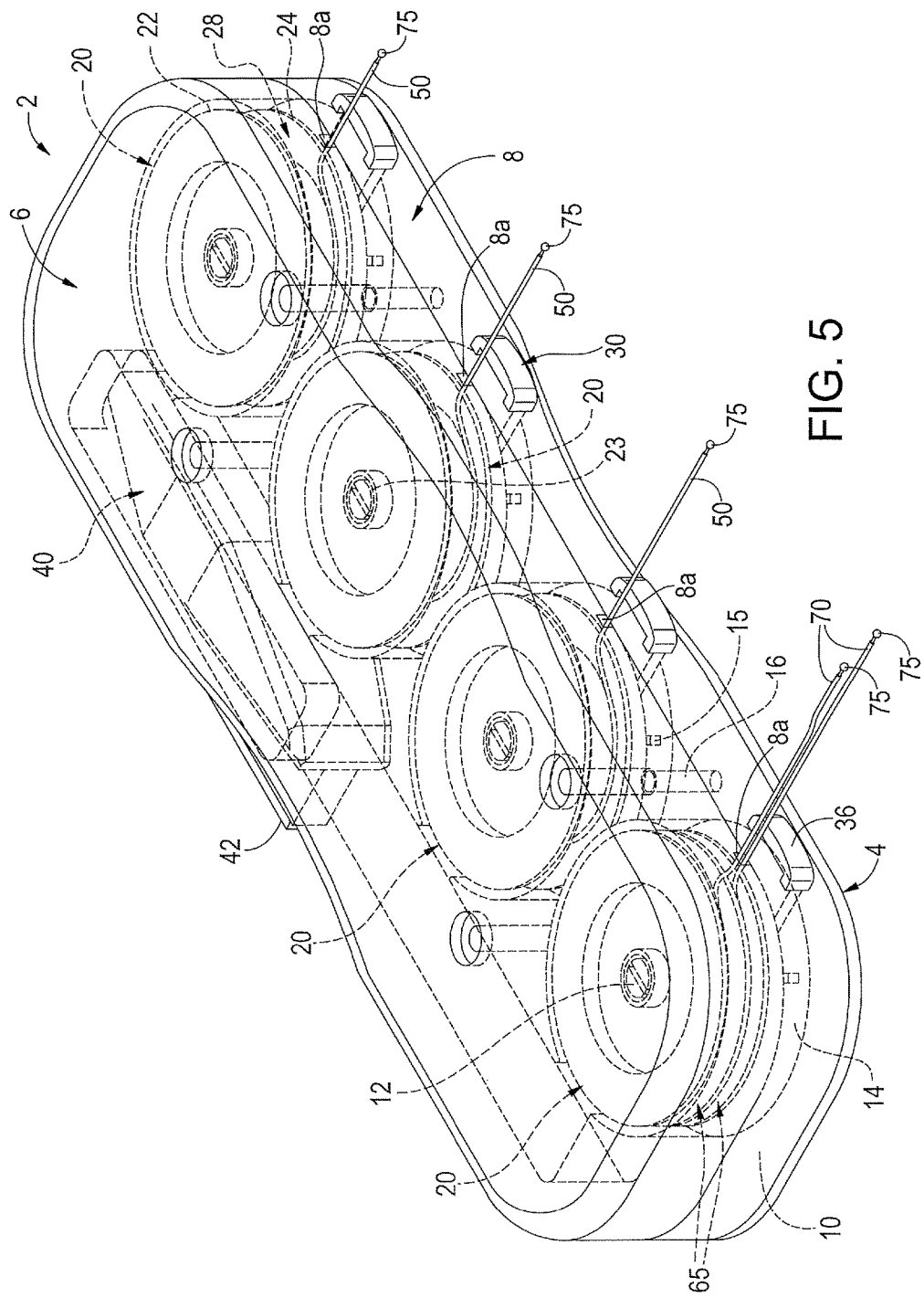
FIG. 5 shows a perspective view of one embodiment of the device.

The primary group comprises an intermediate retraction element 65 associated with the primary electrically conductive elements 70, both shown in FIG. 5. The intermediate retraction element 65 shown in FIG. 5 includes a pair of retraction elements stacked vertically, one on top of the other, each retraction element having a central bore that fits around support member 12. Each retraction element of the intermediate retraction element 65 has an upper and lower base defining a channel for receiving a primary electrically conductive elements 70. The primary electrically conductive elements 70 exit the housing through opening 8A and comprise a first end adapted to engage a sensor 75 and a second end that is in communication with output 40, either directly or indirectly.

What is claimed:

1. An apparatus for conveying electrical signals, the apparatus comprising:
  a. three or more electrically conductive elements for transmitting an electrical signal, each of the electrically conductive elements having a first end and a second end, the first end configured to be in electrical communication with a sensor and the second end in electrical communication with an output, wherein at least one of the electrically conductive elements is a primary group, the primary group comprising a plurality of primary electrically conductive elements and an intermediate retraction element;
  b. a housing having a first and second opposed faces, the housing defining an interior space;
  c. a primary retraction element associated with each electrically conductive element not in the primary group for movably retaining each electrically conductive element, the primary retraction element located in the interior space and an intermediate retraction element associated with the primary electrically conductive elements, the intermediate retraction element located in the interior space for movably retaining the primary electrically conductive elements; and wherein each electrically conductive element is independently moveable between a first stored position and a second in use position and the primary electrically conductive elements of the primary group are moveable between the first stored position and an intermediate position as a group and are moveable between the intermediate position and the second in use position individually.

2. The apparatus of claim 1, wherein the primary retraction element comprises a base, the base comprising an interior channel bounded, at least partially, by two opposing guide flanges.

3. The apparatus of claim 1, wherein the primary retraction element is built for rotational movement about a central member and is in communication with a biasing element.

4. The apparatus of claim 1, wherein the sensor is an electrode.

5. The apparatus of claim 1, the primary retraction element comprises a stop element.

6. The apparatus of claim 1, wherein the output transmits the electrical signal to a monitoring device.

7. The apparatus of claim 1, wherein the primary electrically conductive elements are configured to be positioned on a subject in an area group.

8. The apparatus of claim 1, wherein the housing is a part of a monitoring device.

9. The apparatus of claim 1 comprising at least 4 electrically conductive elements.

10. The apparatus of claim 1 comprising at least 5 electrically conductive elements.

11. The apparatus of claim 1 comprising at least 6 electrically conductive elements element.

12. A medical device, the medical device comprising:
   a. three or more electrically conductive elements for transmitting an electrical signal, each of the electrically conductive elements having a first end and a second end, the first end configured to be in electrical communication with a sensor and the second end in electrical communication, directly or indirectly, with the medical device, wherein at least one of the electrically conductive elements is a primary group, the primary group comprising a plurality of primary electrically conductive elements and an intermediate retraction element;
   b. a primary retraction element associated with each electrically conductive element not in the primary group for movably retaining each electrically conductive element, the primary retraction element located in an interior space of the medical device and an intermediate retraction element associated with the primary electrically conductive elements, the intermediate retraction element located in the interior space for movably retaining the primary electrically conductive elements;
   wherein each electrically conductive element is moveable between a first stored position and a second in use position and the primary electrically conductive elements of the primary group are moveable between the first stored position and an intermediate position as a group and are moveable between the intermediate position and the second in use position individually.

13. The medical device of claim 12, wherein the primary retraction element comprises a base, the base comprising an interior channel bounded, at least partially, by two opposing guide flanges.

14. The medical device of claim 12, wherein the primary retraction element is configured to rotational movement about a central member and is in communication with a biasing element.

15. The medical device of claim 12, wherein the primary retraction element comprises a stop element.

16. The medical device of claim 12, wherein the medical device transmits the electrical signal to an output device.

17. The medical device of claim 12, wherein the primary electrically conductive elements are configured to be positioned on a subject in an area group.

* * * * *